United States Patent [19]

King et al.

[11] Patent Number: 4,578,056
[45] Date of Patent: Mar. 25, 1986

[54] PATIENT PHOTOPHERESIS TREATMENT APPARATUS AND METHOD

[75] Inventors: Martin J. King, Largo; Vernon H. Troutner, St. Petersburg, both of Fla.

[73] Assignee: Extracorporeal Medical Specialties, Inc., King of Prussia, Pa.

[21] Appl. No.: 665,833

[22] Filed: Oct. 29, 1984

[51] Int. Cl.⁴ ............................................ A61M 37/00
[52] U.S. Cl. ...................................................... 604/6
[58] Field of Search ............................. 604/4, 5, 6, 20

[56] References Cited

U.S. PATENT DOCUMENTS

3,489,145  1/1970  Judson .................................. 604/6
4,379,452  4/1983  Devries ................................. 604/6
4,464,166  8/1984  Edelson ................................. 604/6

Primary Examiner—Harland S. Skogquist
Attorney, Agent, or Firm—Mark A. Hofer

[57] ABSTRACT

Provided are apparatus and methods of use for extracorporeally treating a patient whereby blood is withdrawn from the patient, separated into a leukocyte enriched portion which, in contact with a photoactivatable reagent, is irradiated and all blood portions being returned to the patient. The preferred apparatus is suitably modified with appropriate tubing sets, valves, pumps, centrifuge and controlling means to perform the patient treatment in three operational phases.

12 Claims, 3 Drawing Figures

PATIENT PHOTOPHERESIS TREATMENT APPARATUS AND METHOD

FIELD OF THE INVENTION

This invention relates to the field of treating cells with photoactivatable compounds and radiation which activates the compound thereby affecting the cells and specifically, relates to clinically useful systems for the extracorporeal treatment of blood cells, especially leukocytes, with UV radiation.

BACKGROUND OF THE INVENTION

It is well-known that a number of human disease states may be characterized by the overproduction of certain types of leukocytes, including lymphocytes, in comparison to other populations of cells which normally comprise whole blood. Excessive or abnormal lymphocyte populations result in numerous adverse effects to patients including the functional impairment of bodily organs, leukocyte mediated autoimmune diseases and leukemia related disorders many of which often ultimately result in fatality.

U.S. Pat. Nos. 4,321,919; 4,398,906; 4,428,744; and 4,464,166 to Edelson describe methods for treating blood whereby the operation or viability of certain cellular populations may be moderated thereby providing relief for these patients. In general, the methods comprise treating the blood with a dissolved photoactivatable drug, such as psoralen, which is capable of forming photoadducts with DNA in the presence of U.V. radiation. It is believed that covalent bonding results between the psoralen and the lymphocyte nucleic acid thereby effecting metabolic inhibition of the thusly treated cells. Following extracorporeal radiation, the cells are returned to the patient where they are thought to be cleared by natural processes but at an accelerated pace believed attributable to disruption of membrane integrity, alteration of DNA within the cell, or the like conditions often associated with substantial loss of cellular effectiveness or viability.

Although a number of photoactivatable compounds in the psoralen class are known, 8-methoxy psoralen is presently the compound of choice. An effective radiation for this compound, and many psoralens in general, is the ultraviolet spectrum in the range of approximately 320 to 400 nanometers, alternatively referred to as the U.V.A. spectrum. As the development of photoactivatable compounds proceeds, it may be expected that changes in the preferred activation radiation spectrum will be necessary. Suitable selection of radiation sources will, of course, increase treatment efficiency and is contemplated as an obvious optimization procedure for use with the inventions disclosed herein.

Although Edelson's methods have been experimentally shown to provide great relief to patients suffering from leukocyte mediated diseases, numerous practical problems required solutions. In particular, Edelson fails to provide a suitable apparatus for applying radiation to the cells, e.g. via a treatment station, in an economical and efficacious manner, or a system for incorporating a treatment station providing for the treatment of a patient in a clinically acceptable format.

Conventional techniques for photoactivating compounds associated with cells have relied on a plurality of devices including flasks, filtration columns, spectrophotometer cuvettes, and petri dishes. The sample to be irradiated is added to the containers and the container placed adjacent to the radiation source. Such systems tend to be laboratory curiosities as they fail to provide the necessary safeguards intrinsically necessary where patient bodily fluids are concerned, particularly since these fluids must be returned to the patient thereby necessitating strict avoidance of contamination. Further, such methods tend to be volume limited, are characterized by many mechanical manipulations and are generally unacceptable from a clinical and regulatory viewpoint. It is an object of the present invention to provide methods and apparatus suitable for use with the Edelson methods to overcome the limitations associated with the conventional expedients.

Copending application U.S. Ser. No. 650,602 of Taylor describes a preferred form of a practical device for coupling the radiation provided by commercially available light sources, such as the so-called "black-light" fluorescent tubes, to cells for treatment by Edelson's photoactivated drug methods. In summary, the disposable cassette described therein comprises a plurality of fluorescent tube-like light sources such as the U.V.A. emitting Sylvania F8TS/BLB bulb, which are individually, coaxially mounted in tubes of larger diameter which are, in turn, coaxially mounted in sealing arrangement within second outer tubes of even larger diameter thereby forming a structure having two generally elongated, cylindrical cavities about each radiation source. The inner cavity preferably communicates with the atmosphere thereby facilitating cooling of the radiation source. The second tube forming the outer cavity further comprises inlet and outlet means for receiving and discharging, respectively, the cells to be irradiated. A plurality of these structures are "ganged" and suitable connections made between inlets and outlets of adjacent members to provide for serpentine flow of cells through each outer cavity. Thus, continuous flow of the cells through the plurality of cavities surrounding the centrally disposed radiation sources facilitates thorough treatment of the cells. Additional, detailed description of the Taylor device may be obtained by direct reference to the aforesaid application.

To be fully practical, however, the Taylor device requires a clinically acceptable instrument to house the device and to provide the cells to be treated in an appropriate form. It is an object of the present invention to provide such a device.

To date and for clinical use-approval related purposes, the Edelson methods have been performed utilizing a generally impractical and unwieldy apparatus consisting of a large, desk-size metal box containing a series of flexible, relatively transparent plastic bags through which patient blood was pumped. As the blood flowed through each bag, it was irradiated on either side by a plurality of ultraviolet emitting, standard sized, "fluorescent" type tubes housed within the box. Blood flow was generated by means of a separate pump located nearby and connected to the plastic bags as well as source and drain reservoirs by flexible tubing.

Prior to treatment, it has been found preferable to perform leukocyte enriching operations for the purpose of removing substantial portions of red blood cells from the treatment circuit. With the preliminary experimental apparatus, leukocyte enrichment was obtained by centrifuging batch quantities of blood in large volume centrifuge tubes and then dispensing the supernatant plasma into the source bag for treatment. Thus, the Edelson methods have been carried out to date via a cumbersome series of labor intensive, error-prone steps, often exposing the patient's blood to numerous potential sources of contamination during its travels to and from equipment, none of which was designed to optimize the Edelson procedures. Excessive time delays and extensive mechanical manipulations were further exacerbated by the typically divergent locations of various pieces of equipment, necessitated by their space consuming construction. These considerations have resulted in lengthy treatment times and, due to the numerous physical manipulations required, have concommittantly and unacceptably increased the risk of loss or contamination of patient's blood.

It is an object of the present invention to provide methods and apparatus for increasing patient safety thereby also raising his comfort level as well as meeting regulatory acceptability standards.

It is another object of the present invention to provide a complete treatment system which contains all the elements necessary for the withdrawal, separation, and treatment of the patient's blood in a compact and clinically acceptable size and to provide the system in a mobile and automated format thereby reducing the risk of inadvertent contamination while concurrently facilitating the ease with which treatment may be given.

It is still another object of the present invention to provide a suitably automated instrument which can be monitored and operated by less trained personnel thereby lowering treatment costs in accordance with the recently enacted fiscal policies.

It is yet still another object to provide a treatment system suitable for use in the clinical arena whereby the acceptability of the Edelson procedures may be augmented so that a greater number of patients may be meaningfully treated.

BRIEF DESCRIPTION OF THE DRAWINGS

These and still other objects of the invention will become apparant upon study of the accompanying drawings wherein.

SUMMARY OF THE INVENTION

In accordance with the principles and objects of the present invention there are provided methods for extracorporeally photoactivating a photoactivatable reagent in contact with blood cells comprising the steps of collecting and separating on a continuous basis blood from a patient while the patient is connected to the apparatus, returning undesired blood portions obtained during separation, disconnecting the patient from the treatment system while the desired portion is photoactivatably treated whereupon the thusly treated cells are returned to the patient. Thus, the present invention seeks to broadly maximize a patient's safety as well as optimize procedurally the various aspects of such photoactivation treatment by breaking the entire procedure down into three phases or modes. The apparatus, in the first mode, collects and separates blood on a continuous basis as it is withdrawn from the patient and to return unwanted portions to the patient while the patient remains connected to the apparatus. Thereafter, prior to energizing the irradiation sources for photoactivating the photoactivatable reagent in contact with the desired blood portion, the patient is disconnected from the machine thereby removing him from a potential source of harm, the high voltages associated with energizing the irradiation sources. Following photoactivation, the treated cells may then be facilely returned to the patient utilizing a variety of techniques, the preferred being a simple drip chamber gravity feed infusion line.

Figure 1:
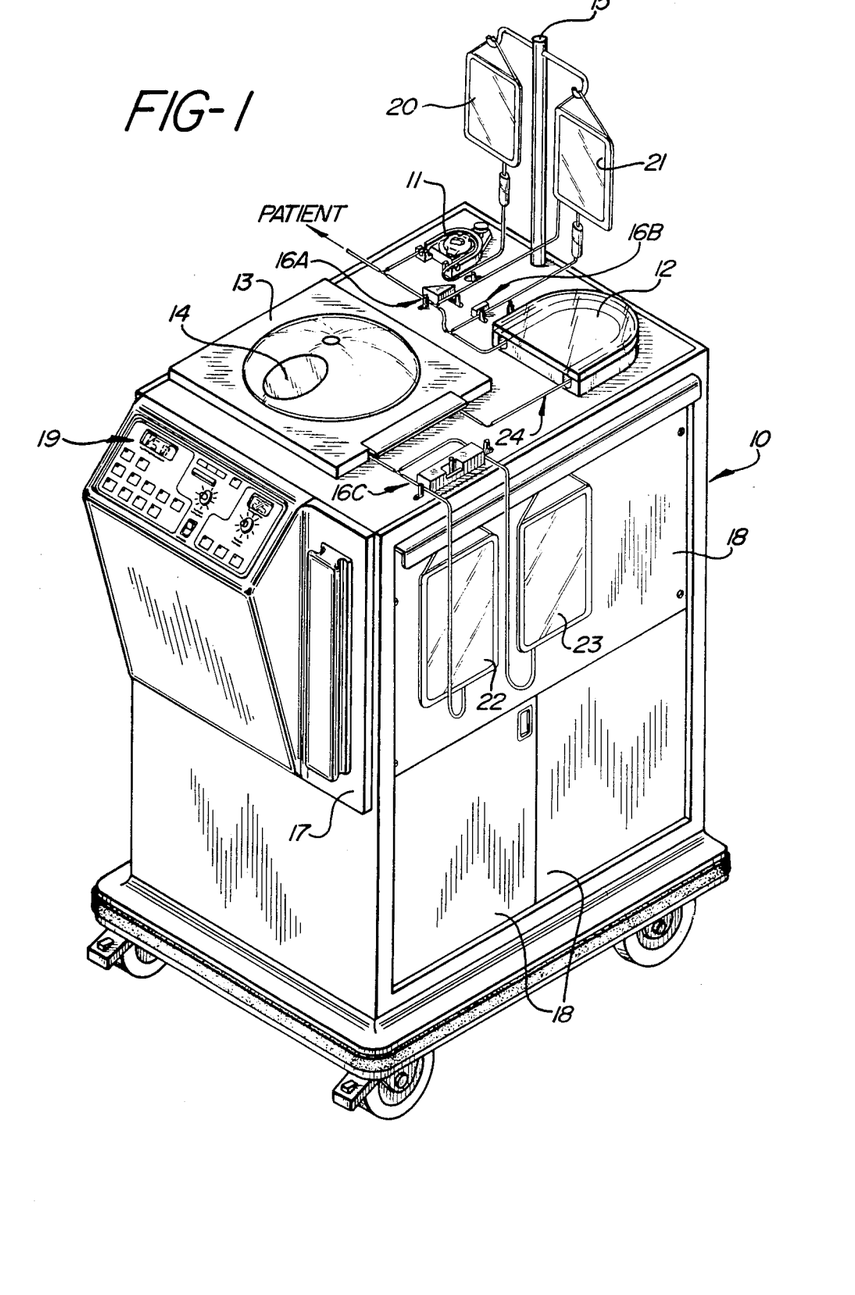
FIG. 1 illustrates a preferred configuration of the system in the collection and separation mode.
Figure 2:
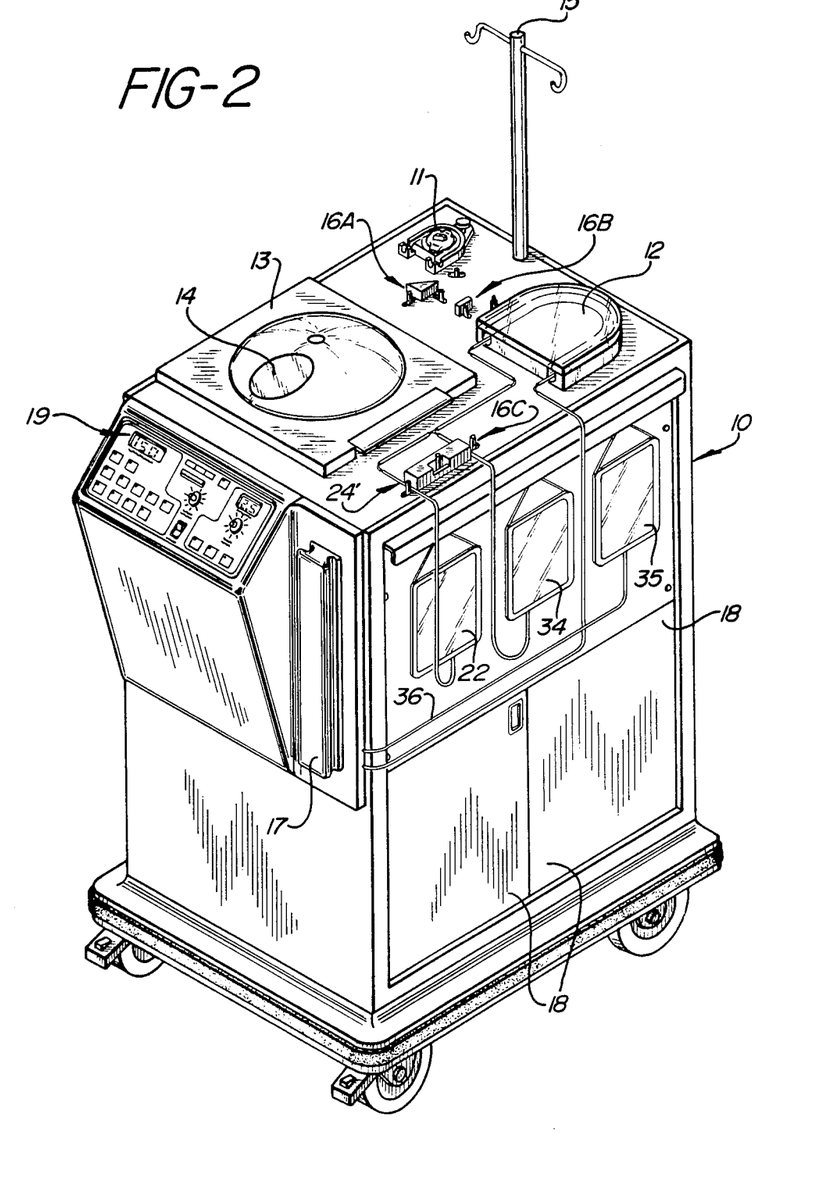
FIG. 2 depicts the system in the treatment mode.
Figure 3:
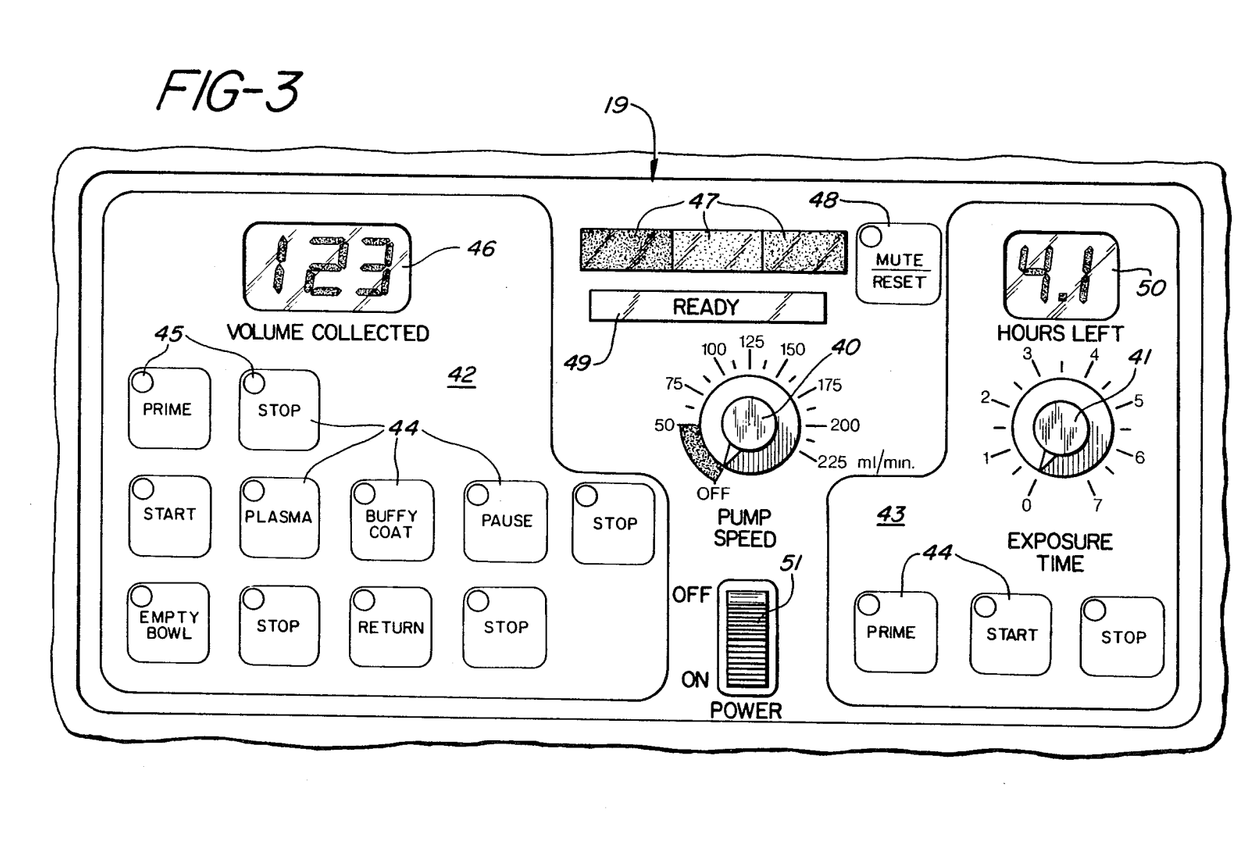
FIG. 3 shows the control panel for the system.

FIGS. 1, 2, and 3 show various aspects of the apparatus developed for extracorporeally treating a patient based in part upon the scientific discoveries of Edelson. The design, construction and operation of the apparatus 10 is the result of a number of separate inventions some of which form the subject matter of copending commonly assigned applications including U.S. Ser. No. 665,834 to Goss entitled "Three Phase Irradiation Treatment Process"; U.S. Ser. No. 665,831 to King entitled "Electronic Control Methods for Puvapheresis Apparatus"; U.S. Ser. No. 665,827 to Troutner entitled "Valve Apparatus for Photoactivation Patient Treatment System"; U.S. Ser. No. 665,832 to King entitled "Automated Photopheresis Blood Portion Control Methods and Apparatus"; and U.S. Ser. No. 665,817 to Troutner entitled "Cassette Drawer Assembly for Photoactivation Patient Treatment System", the relevant parts of which are fully incorporated herein by reference.

The operation of the device and performance of the methods can be divided into three basic phases, two of which are depicted in part by FIGS. 1 and 2. The first phase is shown substantially in FIG. 1 wherein the patient is connected, at the point shown, such as by veni-puncture or like methods well-known and developed to a high degree in the dialysis arts. Patient blood, as it flows to the apparatus 10 (alternately referred to herein as the puvapheresis apparatus or system) is preferably infused, under control of pump 11, with an anticoagulant agent contained in container 20 hung from stand 15. Control of the flow of patient blood to the remainder of apparatus 10 is controlled largely by clamping means 16a which has the dual function of also controlling flow in the reverse direction as well as flow to return container 21; clamp 16a acting as an "or" valve. Normally the blood flows through tubing 24 through blood pump 12 into a continuous centrifuge 13. This continuous centrifuge, available commercially from suppliers such as Dideco and others, is preferably capable of continuously separating blood based on the differing densities of the individual blood components. "Continuously", as used herein means that as blood flows into the centrifuge through line 24, it accumulates within the rotating centrifuge bowl and is separated so that low density components are emitted after a certain minimum volume has been reached within the centrifuge bowl and as additional blood is added. Thus, the continuous centrifuge in effect acts as a hybrid between a pure online system and a pure batch system. This occurs because the centrifuge bowl has a capacity to hold most, if not all, of the most dense portion, typically erythrocytes or red blood cells while emitting lower density portions such as plasma and leukocytes (white blood cells) as whole blood is continuously added. At some point, however, the reservoir volume of the centrifuge is filled with the higher density components and further separation cannot be effectively obtained. Prior to that point, the operator, by viewing the uppermost portion of the centrifuge bowl through magnifying observation point port 14 of the centrifuge cover, can detect qualitatively when the centrifuge emits plasma (as opposed to priming solution), leukocyte enriched portions and nonleukocyte enriched portions such as erythrocytes. Based on the operator's observations, he or she enters through control panel 19 (specifically via panel portion 42) the identification of the individual blood portions as they are emitted from the centrifuge. Based on this information entered by keys 44 (e.g. PLASMA, BUFFY COAT or leukocyte enriched portion) on control panel 19, (shown in FIG. 3) the apparatus 10 controls valve mechanism 16c to direct the leukocyte enriched portion and a predetermined volume of plasma into plasma-leukocyte enriched container 22 while excess plasma, air, priming fluids, erythrocytes etc. are directed to container 23.

Once the centrifuge is no longer capable of further separation due to the attainment of its capacity, the operator directs that the bowl be emptied (see FIG. 3) by suitable data key entry and the contents of container 23 and centrifuge 13 are advantageously pumped into return container 21 by means of pump 12 under the control of valves 16a and c. The foregoing steps may be repeated a number of times or cycles before the desired volume of leukocyte enriched blood and plasma is obtained for further treatment, in each instance the undesired portions being first collected in container 23 and then pumped to return container 21.

Between cycles, the erythrocyte enriched portion which is pumped into return bag 21 is gravity fed back to the patient through a drip infusion operation and controlled by valve 16b. It is preferred that gravity feed be employed rather than pumping the blood back to the patient via pump 12 in order to avoid potential pressurization problems at the infusion insertion site at the patient, and also to avoid foaming or other air related dangers.

As may be already appreciated, when initially set up, line 24 may be expected to contain sterilized air which is preferably removed by suitable priming operations utilizing the anti-coagulation agent in container 20; both the air and the priming solution being collected in container 23.

Also to be noted is the predetermination of the desired leukocyte enriched volume and plasma volume to be collected within container 22 as well as the number of cycles to be employed to collect same. These volumes are selected largely in accorance with the individual volume capacities of the containers as well as the treatment cassette to be described later. Accordingly, these volumes are selected in order to preferably optimize handling efficiency and to ensure patient safety. For instance, one preferred selection would be as follows: 250 ml total buffy coat or leukocyte enriched portion and 300 ml of plasma to be collected within container 22. This might require any number of cycles preferably on the order of say three or four bearing in mind that the more cycles that are selected, the lower the total volume of blood withdrawn from the patient at any one time, within minimum capacity limits of the centrifuge bowl, thus increasing the patient's capacity to withstand temporary blood volume depletions and the treatment procedure in general. Alternately, more cycles will also permit more discriminating selection of leukocyte enriched blood as it is emitted from the centrifuge. The buffy coat and plasma volumes as well as the number of cycles are typically physician selected and accordingly, the controls governing the selections are preferably placed within the apparatus 10, such as behind doors 18 where their inadvertent alteration may be avoided especially since no operator interaction is ordinarily required with respect to these data inputs.

Referring now to FIG. 2, a second tubing set for the second operational mode shown with leukocyte enriched container 22 connected via tubing line 24' through valves 16c, blood pump 12 to the treatment cassette behind door 17 with a return line 36 to reservoir container 35. The tubing set for the second mode will also preferably include container 34 for providing a priming solution for evacuating air contained within tubing set 24' and the cassette treatment module, described in copending application of Taylor, U.S. Ser. No. 650,602. In brief summary, the Taylor cassette comprises a plurality of ganged cylindrical cavities each of which is concentrically mounted around a cylindrical irradiation source in turn powered by apparatus 10.

In operation, and with respect to FIG. 3, the exposure time on the right hand portion of the panel 43 is set in accordance with physician determined criteria via knob 41. The central control means of the apparatus 10, calculates and displays (50) via central processing unit and memory stored software, the exposure time remaining at the onset of irradiation treatment and as the treatment progresses. Section 43 of the control panel also includes three operator controlled entry data keys 44 whereby the first step, PRIME, may be initiated whereupon the priming solution from container 34 is pumped via blood pump 12 through tubing set 24' and the treatment cassette emptying into reservoir 35. Thereafter, the operator, by pushing START in section 43, initiates actual photoirradiation treatment whereupon the leukocyte enriched portion of the blood collected within container 22 is pumped through tubing set 24' in accordance with suitably altered valve 16c through blood pump 12 to the treatment cassette and return line 36 to reservoir 35.

The treatment cassette container assembly 17 further comprises bubble detectors connected to the central control means for detecting the presence of air about to enter the treatment cassette. The presence of the air indicates the complete evacuation of container 22 and signals the end of the first treatment pass. Thereafter, the central control means reverses the direction of blood pump 12 which draws blood from container 35 back through the treatment cassette through the blood pump and to container 22. The actual direction of the blood flow through the treatment cassette is of no significance as flow in either direction is equally photoactivated. An advantage gained by reversing direction (as opposed to constant cycling in the same direction) is the hydrodynamic mixing of blood as it is passed through the container. Such mixing is thought to result in a more thorough treatment of the individual cells because the statistical probability that each cell will be individually contacted by irradiation is increased. This process of blood flow until container 22 or 35 is emptied and then reversal thereof is continued until the desired exposure time is attained. At that point, the treated blood portion is then preferably returned to blood container 22 and the tubing set 24' discarded. Container 22 is then ideally removed to stand 15 and a third tubing set connected to container 22 for reinfusion of the treated blood portion into the patient. During the second operational mode when the actual irradiation treatment is performed as depicted by FIG. 2, the patient is preferably disconnected from the machine thereby adding to his (or her) comfort level by permitting him freedom to move about but also concommitantly, increasing his safety level as he (or she) is not connected to the machine when the high voltages, necessary to drive the irradiation sources, are present.

To further decrease the risk of contamination to the patient blood and blood portions, each time a connection is made or broken, it is preferably only done once. Thus, container 22 would have three connection ports; one for the first mode collection of the leukocyte enriched blood portion, one for the second mode treatment phase shown by FIG. 2, and the third for the third operational mode wherein treated blood is reinfused to the patient.

With particular reference to FIG. 3, the control panel 19 of the apparatus 10 is shown with the key board entry buttons 44 each ideally having a light 45 which, when lit, preferably indicates the stage of the operation. As will be noted, the key board entry buttons 44 are preferably placed in sequential order thereby assisting the operator in learning the system and performing the steps in the correct order. Indeed, the central control means will preferably be programmed to prevent out of step sequences from being attempted. Display 46 indicates the volume of leukocyte enriched blood collected in container 22. Although not shown, there is preferably also included a manual override switch contained within apparatus 10 such as behind access doors 18 (see FIGS. 1 and 2) for allowing an experienced operator to select any step out of sequence in the unlikely circumstance that such may be necessary to return all blood to the patient in the event of a machine failure.

The central portion of panel 19 contains power switch 51 as well as blood pump speed control 40 whereby the operator may select the speed with which the blood is withdrawn from the patient and pumped through the system during either collection or treatment phases. Also included in the central section are lights 47 and 49. Alphanumeric display 49 indicates alarms and status regarding the machine's sequential operations. Status lights 47 are preferably provided in green, yellow, and red colors in order to provide at a glance the overall operating status of apparatus 10. Further included is a mute/reset button 48 for quieting an audible alarm activated in the event an alarm condition occurs and operator input is required.

Other features may be readily apparent from the drawings such as the preferable inclusion of casters and caster brakes for enhancing the mobility of the apparatus. Further, upper access door 18 will preferably include mechanical means for assisting in the securement of containers 22, 23, 34, and 35. It may also optionally be outfitted with a transparent or translucent opening in the area beneath container 22 for providing at a glance information regarding the illumination status of the irradiation treatment cassette during the treatment phase. For instance, if the window is of sufficient size, the operator may readily determine that each irradiation source within the treatment cassette is illuminated as desired. Naturally, the material comprising such window is preferably selected in order to contain harmful radiation, if any, within apparatus 10.

Safety of the patient as well as efficiency of operation can be maximized by reducing the operation into three clearly demarcated phases. The first phase, with the patient connected to the apparatus, collects blood from the patient and separates it into the desired leukocyte enriched portion and plasma. The remaining blood portions, essentially erythrocyte enriched, and excess plasma, if any, obtained from the separation processes are then reinfused to the patient. The patient is then disconnected from the apparatus and the tubing set, used during the collection or first phase, discarded with the exception the container 22 having the leukocyte enriched blood portion.

The second phase of the operation then commences with the connection of the irradiation tubing set including the treatment cassette of Taylor or other similar irradiation treatment module. The irradiation tubing set will further preferably contain a reservoir such as container 35 shown in FIG. 2 and in the most preferred embodiment, also container 34 having a priming solution. The leukocyte enriched portion, mixed with a predetermined volume of plasma, is then irradiated in the treatment cassette or other suitable irradiation station until a predetermined level of photoactivation is achieved. The irradiated blood portion is then preferably returned to the original leukocyte container 22 and the second phase terminated upon disconnection of container 22 from the irradiation tubing set. The tubing set is then preferably discarded as it is no longer used in the three phase patient treatment procedure and indeed, is preferably not used again in order to avoid possible interpatient contamination or other sterilization related problems.

The third phase comprises the connection of an infusion tubing set to container 22 for return of the irradiated leukocyte enriched blood portion to the patient. This is preferably accomplished by simple gravity feed such as by the attachment of the container to stand 15 on the apparatus 10 or to any standard I.V. stand as may be suitable and appropriate in the circumstances.

By splitting the process into these three broad phases, a number of unobvious advantages are gained. Foremost among them, is the attainment of patient safety by preventing at all times the possible electrical shock hazard to the patient from the high voltages required for standard irradiation sources. This is prevented because at no time during the first phase, i.e. the only phase during which the patient is connected to the apparatus 10, is there a possible fluid connection between the patient and the irradiation treatment station or cassette. Such a fluid connection (indeed only possible if a leakage should occur in the area of the treatment cassette) with the irradiation electrical power source can only occur during the second phase by which time the patient has already been disconnected from the apparatus. Furthermore, the tubing set complexity is reduced by providing three separate tubing sets for each phase of the operation thereby reducing costs of the tubing set, reducing the difficulty in their manufacture, and reducing the difficulty in their attachment and installation on apparatus 10.

Another unobvious result from dividing the procedure into three phases is the reduction of apparatus complexity in the form of fewer valves and pumps which would otherwise be required. For instance, if one attempted to combine the first and second phases, the resulting complicated tubing set would require multiple pumps and many more additional valves for separately controlling the flow through the centrifuge and the flow through the irradiation treatment station since these could not now be accomplished with a single pump. Complicated tubing sets and numerous pumps and valves greatly increase the risk of breakdowns as well as leakage and contamination to the patient blood thereby undermining the value of the treatment and ultimately dispensing with the objects and principles of the present invention.

Still another problem is solved by the instant invention and this concerns the development of an apparatus and treatment system which may be readily performed by technicians without the need of advanced degrees or other detailed instruction. By breaking the system into three phases, at least two of which are clearly separated on the control panel 19, and the third not requiring the apparatus at all, the technician is more readily capable of grasping the individual sequence of steps and accomplishing the desired irradiation treatment safely, efficaciously, and rapidly. Thus, the complement of personnel capable of performing the photoactivation patient treatment procedures is expanded. It is hoped that this will enhance the acceptability of the Edelson procedures within the clinical environments thereby benefiting more patients.

The three phase process of the instant invention facilitates the design of a patient treatment assembly 10 which has fewer parts, is more easily manufactured and thus available at lower cost, an important criteria in view of recent fiscal constraints placed on the clinical environment. Further, the instant invention allows for simpler tubing sets which in turn may be more readily manufactured and offered at lower cost.

As previously indicated, this invention includes three tubing sets which are individually dedicated to one of the operating phases of the photopheresis apparatus. The first tubing set is preferably designed to be solely utilized for the blood collection and separation mode; the second tubing set for the treatment mode; and the third tubing set for reinfusion of the treated leukocyte enriched blood to the patient. The tubing sets comprise, in the most preferred embodiment, clear flexible plastic tubing such as that available under the name Tygon ™ or other similar materials such as have been employed in the dialysis fields.

The most preferred first tubing set comprises a first container for receiving the leukocyte enriched blood and plasma emitted by the centrifuge, and a second container for receiving excess plasma and nonleukocyte enriched fluids also emitted from the centrifuge. Such nonleukocyte enriched fluids could include, for instance, priming fluids used to evacuate air spaces within the tubing in the centrifuge, plasma emitted from the centrifuge which exceeds the predetermined plasma volumes as well as erythrocyte enriched blood portions which may be emitted from the centrifuge prior to the end of the collection and separation cycle or combination thereof. Prior to the initiation of the next cycle, the materials contained within the second container are preferably returned to the patient in order to advantageously refrain from withdrawing too much blood from the patient at any one time. It has been found efficacious for this purpose to employ a return container for receiving the contents of the second container and also for receiving the contents of the centrifuge bowl as it is emptied. This container is ideally elevated such as by hanging it on stand 15 so that reinfusion to the patient may be accomplished by standard gravity feed through a drip tube. Such a method, of course, obviates the need for foam and bubble detectors as well as pumps carefully regulated to prevent undue pressure at the patient infusion site.

The ideal collection and separation tubing set, or first tubing set, will also be adapted for connection with an additional container which may be supplied with or separately from the first tubing set, said separate container for providing an anti-coagulation agent. Such agents, e.g. heparin, citrate, EDTA (ethylenediaminetetraacetic acid) and the like are well-known in the art and assist in preventing unwanted coagulation as blood flows through the tubing and other various aspects of the instant invention. Further, the anti-coagulation agent may be employed as a priming solution for removing unwanted air spaces in the tubing set and the centrifuge bowl.

The instant invention also includes a second tubing set for use during the second mode of operation wherein the leukocyte enriched blood portion is irradiated in order to photoactivate the photoactivatable agent pursuant to the Edelson technology. Accordingly, it has been found advantageous to employ a second tubing set comprising an irradiation cassette for applying photoactivating radiation such as, in the most preferred embodiment, the ganged cassette irradiator of Taylor. The second tubing set further comprises tubing means for connection between the first container of the first tubing set (retained in the transition from first to second operating modes) and the irradiation cassette means. The ideal second tubing set further includes an additional container for providing priming solution for evacuating air spaces within the second tubing set and the irradiation cassette as well as temperature transfer tubing segments for contact with blood temperature sensors in th drawer assembly 17.

The second mode of operation is ideally completed upon the return of the irradiated blood portions to the first container and the retention of the first container for the third mode of operation. During this third phase, the irradiated blood from the first container is returned to the patient and again, this is preferably accomplished by gravity infusion through a drip tube. Accordingly, the ideal third tubing set comprises a gravity drip tube for connecting the first container to the patient.

It is preferable that all containers are configured so that when connections are made between tubing and containers such as those made with the first container during each of the three modes of operation, such connections will be made at a separate port so that each port is preferably employed only once thereby inhibiting or preventing unintentional contamination.

After a careful review of the foregoing description, accompanying drawings and related applications cited herein, one skilled in the art will readily appreciate that numerous changes may be made without substantial alteration of or deviation from the spirit or scope of the present invention.

What is claimed is:

1. Apparatus for use in a patient treatment system wherein blood, in contact with a photoactivatable reagent, is collected from said patient, centrifuged to provide a leukocyte enriched portion which is irradiated for activating said reagent, all portions including the irradiated portion being returned to said patient, said apparatus comprising:
   infusion pump means for controlling the addition of anticoagulation agent means to said patient's blood;
   receiving means for receiving an irradiation cassette adapted to provide said photoactivating irradiation;
   continuous centrifuge means for separating patient blood into at least a plasma portion and a leukocyte enriched portion, said centrifuge means including a revolution sensor for monitoring rotation;

blood pump means for pumping blood from said patient to said centrifuge, said blood pump means including revolution counter means and having known pumping characteristics whereby blood volume pumped may be determined;

central control means for regulating said infusion pump means, said receiving means, said continuous centrifuge means and said blood pump means whereby blood withdrawn from said patient, is contacted with said anticoagulant agent means, separated into a leukocyte enriched portion which, while in contact with said photoactivatable reagent, is irradiated prior to its return to the patient.

2. The patient treatment apparatus as set forth in claim 1 further comprising:

a first valve for controlling flow of non-leukocyte enriched fluids from said blood pump to a return container adapted for returning said fluid to said patient;

a second valve for controlling and directing the infusion of said fluid from said return container to said patient; and a third valve for directing the flow of plasma and leukocyte enriched blood portion, and the flow of excess plasma from said centrifuge to separate containers.

3. A blood collection and separation tubing set for use in a patient treatment system wherein blood is collected from said patient, centrifuged to provide a leukocyte enriched portion which, in contact with a photoactivatabable reagent, is irradiated for activating said reagent, all blood portions including the irradiated portion being returned to said patient, said collection tubing set comprising:

a first container for receiving leukocyte enriched blood and plasma;

a second container for receiving excess plasma and nonleukocyte enriched fluid;

a return container having an inlet for receiving the contents of said second container and an outlet for returning same to said patient; and tubing means for sterilly connecting said foregoing containers and adapted for optional connection to an anticoagulation container for providing anticoagulation means to said patient blood.

4. A blood treatment tubing set for use in a patient treatment system wherein blood is collected from said patient, centrifuged to provide a leukocyte enriched blood portion which, in contact with a photoactivatable reagent, is irradiated for activating said reagent, all blood portions including the irradiated portion being returned to said patient, said treatment tubing set comprising:

irradiation cassette means for receiving said leukocyte enriched blood portion and adapted to apply photoactivating radiation thereto;

a blood reservoir for receiving said leukocyte enriched blood passing through said irradiation cassette means and for returning blood to said cassette means whereby said leukocyte enriched blood may be irradiated again; and tubing means for sterilly connecting said blood reservoir and said irradiation cassette means and adapted to receive said leukocyte enriched blood to be irradiated.

5. Apparatus for use in an extracorporeal patient treatment system wherein blood is collected from said patient, centrifuged to provide a leukocyte enriched portion which, in contact with a photoactivatable reagent, is irradiated for activating said reagent, all blood portions including the irradiated portion being returned to said patient, said apparatus comprising:

infusion pump means for controlling the addition of an anticoagulation agent to said patient's blood;

continuous centrifuge means for separating patient blood into at least plasma, and a leukocyte enriched portion;

a first tubing set including:
 a first container for receiving said leukocyte enriched blood and plasma;
 a second container for receiving excess plasma and non-leukocyte enriched fluids;
 a return container having an inlet for receiving the contents of said second container and the contents of said centrifuge and an outlet for returning same to said patient and;
 first tubing means for receiving said anticoagulation agent and for sterilly communicating blood sterilly from said patient to said centrifuge means, to said first container, to said second container and to said return container;

a second tubing set including:
 irradiation cassette means for applying photoactivating radiation to said photoactivatable reagent; and
 second tubing means for sterilly communicating blood between said first container and said cassette means blood pump means for pumping blood from said patient, through said first tubing set and said centrifuge during a first operating phase, and for pumping leukocyte enriched blood through said second tubing set during a second operating phase, said blood pump means including monitor means wherby the volume pumped may be determined;

central control means for electronically communicating with:
 a first valve associated with said return container inlet for controlling fluid flow into said container;
 a second valve associated with said return container outlet for controlling and directing the return of fluids from said return container to said patient;
 a third valve for controlling and directing blood portions from said centrifuge to said first or second container;
 said blood pump means and said blood pump monitor means whereby the volume pumped may be monitored and the volume and direction of blood flow controlled;
 said continuous centrifuge means for sensing rotation;
 said infusion pump for regulating the addition of anticoagulation agent to said patient blood; and
 manual control means for accepting a predetermined leukocyte enriched blood volume and plasma volume; and
 memory means for providing treatment sequence procedures and operating parameters to said central control means;

whereby in accordance with said treatment sequence procedure and operating parameters from said memory means, said central control means controls the withdrawal of blood from a patient, the addition of anticoagulation agent thereto, the centrifugation thereof, and the collection and irradiation of predetermined plasma and leukocyte enriched blood portion, and the return of the blood portions to the patient.

6. The extracorporeal patient treatment apparatus set forth in claim 5 wherein said centrifuge means further comprises safety cover interlock means connected to said central control means for preventing operator access to said centrifuge while said centrifuge is rotating.

7. The extracorporeal patient treatment apparatus set forth in claim 5 wherein said second tubing set further comprises a reservoir container for receiving blood from said irradiation cassette means and for returning blood to said irradiation cassette means when blood flow through said irradiation cassette means is reversed.

8. The extracorporeal patient treatment apparatus set forth in claim 7 wherein said second tubing set further comprises a priming container adapted for connection with said second tubing set means for supplying a priming solution useful for removing air from said irradiation cassette means.

9. A method for treating a patient for use in an extracorporeal treatment system wherein blood is treated with a photoactivatable reagent, irradiated, and returned to the patient, said system including an electronic central control means for controlling the sequence of treatment steps and automatically monitoring the acquisition and treatent of blood volumes in accordance with preset indices, said method comprising the steps of:
(a) connecting said treatment system to said patient whereby blood may be withdrawn from and returned to said patient;
(b) withdrawing blood from said patient;
(c) infusing blood from said patient with an effective anticoagulant;
(d) pumping said anticoagulated blood to a continuous centrifuge for separating said blood into at least a plasma enriched portion and a leukocyte enriched portion;
(e) directing, in accordance with predetermined volume parameters, said plasma and said leukocyte enriched portion to a first container;
(f) further directing excess plasma, if any, and non-leukocyte enriched fluids from said centrifuge to a second container;
(g) returning the contents of said second container to the patient;
(h) performing steps b–g until the predetermined volume of leukocyte enriched blood portion has been obtained in said first container;
(i) connecting said first container to irradiation cassette means having a at least one radiation source and at least one chamber for receiving said leukocyte enriched blood and exposing it to radiation from said radiation source, said chamber substantially surrounding said radiation source;
(j) energizing said radiation source and passing the contents of said first container through said chamber of said irradiation cassette means whereby said reagent is photoactivated; and then
(h) returning said irradiated leukocyte enriched blood portion to said patient.

10. The treatment method provided in claim 9 wherein the step of passing the contents in step (j) is performed until the amount of radiation reaches a predetermined level.

11. The treatment method provided in claim 10 wherein step (g) further includes the steps of emptying the centrifuge and combining the centrifuge contents with the contents of the second container and returning the combined contents to the patient.

12. The treatment method provided in claim 11 wherein the combining step includes transferring the contents of the second container and the contents of the centrifuge to a third container and then returning the combined contents to the patient.

* * * * *